(12) United States Patent
Woodward et al.

(10) Patent No.: US 7,204,152 B2
(45) Date of Patent: Apr. 17, 2007

(54) APPARATUS AND METHOD FOR FATIGUE TESTING

(75) Inventors: Colin J Woodward, Derby (GB); Martin McElhone, Derby (GB); James S Crabtree, Derby (GB); Paul A Greenacre, Derby (GB)

(73) Assignee: Rolls-Royce plc, London (GB)

( * ) Notice: Subject to any disclaimer, the term of this patent is extended or adjusted under 35 U.S.C. 154(b) by 62 days.

(21) Appl. No.: 11/104,486

(22) Filed: Apr. 13, 2005

(65) Prior Publication Data

US 2005/0252304 A1 Nov. 17, 2005

(30) Foreign Application Priority Data

May 17, 2004 (GB) ................... 0410967.4

(51) Int. Cl.
*G01N 3/00* (2006.01)

(52) U.S. Cl. ............................ 73/794; 73/804; 73/808; 73/810; 73/811; 73/813; 73/815; 73/821; 73/845; 73/865.9

(58) Field of Classification Search ............ 73/794, 73/804, 808, 810, 811, 813, 815, 821, 845, 73/865.9
See application file for complete search history.

(56) References Cited

U.S. PATENT DOCUMENTS

| | | | |
|---|---|---|---|
| 3,690,162 A * | 9/1972 | Stecher .................... | 73/119 R |
| 4,478,086 A * | 10/1984 | Gram ........................ | 73/781 |
| 5,388,464 A * | 2/1995 | Maddison ................. | 73/856 |
| 5,952,581 A * | 9/1999 | Lammers et al. ........... | 73/831 |
| 6,023,980 A * | 2/2000 | Owen et al. ................ | 73/797 |
| 6,247,370 B1 | 6/2001 | Ramaswamy | |
| 6,250,166 B1 | 6/2001 | Dingwell | |
| 6,601,456 B1 * | 8/2003 | Davidson et al. .......... | 73/808 |
| 6,718,833 B2 * | 4/2004 | Xie et al. ................... | 73/812 |
| 6,732,591 B2 * | 5/2004 | Miles et al. ............... | 73/808 |
| 6,813,960 B1 * | 11/2004 | Owen et al. ............... | 73/808 |
| 6,848,311 B1 * | 2/2005 | Hull .......................... | 73/579 |
| 2002/0017144 A1 * | 2/2002 | Miles et al. ............... | 73/808 |
| 2002/0162400 A1 | 11/2002 | Xie | |

FOREIGN PATENT DOCUMENTS

| | | |
|---|---|---|
| FR | 7 631 155 A | 5/1978 |
| GB | 2 282 228 A | 3/1995 |
| SU | 0 966 532 AB | 10/1982 |
| WO | WO 2004/005879 PU | 1/2004 |

\* cited by examiner

*Primary Examiner*—Edward Lefkowitz
*Assistant Examiner*—Freddie Kirkland, III
(74) *Attorney, Agent, or Firm*—W. Warren Taltavull; Manelli Denison & Selter PLLC

(57) ABSTRACT

A method of simulating life of a rotor blade mounting feature mounted in a complementary rotor disc mounting feature comprises the steps of providing two specimen mounting features (37) each having portions defining pressure faces matching in profile respective faces of the rotor blade mounting feature; providing a fixture (38) having two opposed mounting features (39) each having portions defining pressure faces (78) matching in profile respective faces of the rotor disc mounting feature; mounting the specimen mounting features (37) in the fixture mounting features (39); applying a first load to the specimen mounting features (37); measuring a strain in a region (86) of the fixture (38) between the fixture mounting features (39); applying a second load to the fixture (38), the second load being substantially perpendicular to the first load; and controlling the second load in response to the measured strain. A high cycle load may simultaneously be applied to the specimen mounting features (37). Claims are also included for an apparatus (10) for carrying out the method.

14 Claims, 2 Drawing Sheets

APPARATUS AND METHOD FOR FATIGUE TESTING

FIELD OF THE INVENTION

This invention relates to fatigue testing of materials, and more particularly relates to an apparatus and method for simulating fatigue of rotor blade roots in complementary rotor blade slots.

BACKGROUND OF THE INVENTION

Gas turbine engine fan blades, compressor blades and turbine blades are subjected to a combination of low cycle fatigue (LCF) and high cycle fatigue (HCF) stresses during the engine's operation. These LCF and HCF stresses have a detrimental effect on the integrity of the blades. The LCF stresses result from the centripetal force experienced by the blades as they rotate about the engine axis. The HCF stresses result from aerodynamic and other vibration excitation of the blades.

In order to design fan blades, compressor blades and turbine blades that are resistant to fatigue, a good understanding is required of the combination of the steady and alternating stresses to which a blade may be subjected in operation.

The fatigue testing of materials under conditions representative of gas turbine operating conditions is difficult to achieve for blade aerofoil shapes and blade root shapes. Conventional LCF, HCF and fatigue crack growth (FCG) testing on simple specimen shapes have been used to provide mechanical data. Comparisons between these simple specimen shapes and real blades have revealed marked differences in fatigue life. It is known to perform tests on specimens representative of blade shapes, but the behaviour of these specimens does not accurately reflect the behaviour of real blades. Consequently safety factors, typically 50%, are commonly applied to fatigue data.

Dovetail roots are a commonly used method for attaching aero-engine rotor blades to their corresponding disc. They have the advantages of simplicity of manufacture, ease of assembly and high load carrying capability. A dry film lubricant, such as molybdenum disulphide, is commonly applied to the blade and disc dovetail to maintain low friction and prevent damage to the metal surfaces.

During service operation, the rotor blade assembly is subject to a complex loading system, comprising centripetal load, gas load and vibration. Rotation of the fan assembly results in a large load on the dovetail root, due to centripetal acceleration, as the blade tries to pull out of the retention slot. Hoop stresses are generated in the disc rim, as the disc grows under the influence of its own mass and those of the attached blades. In addition, as the fan blade compresses the incoming air, the pressure differential across the blade causes the aerofoil to bend, imparting an additional bending load into the dovetail root. Finally, blade mechanical resonances, and aerodynamic forcing, impose vibratory loading to the dovetail root.

Under the action of these loads, sliding occurs between the blade and disc dovetail, which in combination with the high contact pressures between the two components, can lead to rapid loss of traditional low-friction dry film lubricants. As the coating breaks down, the friction level rises and stress levels in the blade and disc dovetail edge-of-contact region increase. Further wear of the coating leads to metal-to-metal contact between the blade and disc, resulting in heavy frettage and wear of the underlying material. In some cases, interfacial cold welding and plucking can occur, leading to heavy galling and the generation of additional stress concentration features.

These processes, in combination with the applied loads, can lead to the initiation of fatigue cracking at the dovetail edge-of-contact. The underlying component stress field due to centripetal load, gas bending and vibration may then propagate these cracks, resulting in blade or disc failure. In the worst case, where vibration stress levels are high enough to cause crack propagation, failure may occur in a very small number of flights.

Experiments have shown that edge-of-bedding (EOB) fatigue life is critically dependent on the integrity of any anti-frettage coating applied to the blade/disc bedding flanks. Specifically, the friction level on the dovetail contact flank influences fatigue life.

There is therefore a need to provide fatigue data from specimens whose geometry and stress states are more nearly comparable to real blades in order to aid the design of blades resistant to fatigue or to determine more accurately the working life of real blades.

SUMMARY OF THE INVENTION

Accordingly the present invention seeks to provide a novel apparatus and method for the fatigue testing of materials which reduces, and preferably overcomes, the problems set out above.

According to a first aspect of the invention, a method of simulating life of a rotor blade mounting feature mounted in a complementary rotor disc mounting feature comprises the steps of providing two specimen mounting features each having portions defining pressure faces matching in profile respective faces of the rotor blade mounting feature; providing a fixture having two opposed mounting features each having portions defining pressure faces matching in profile respective faces of the rotor disc mounting feature; mounting the specimen mounting features in the fixture mounting features; applying a first load to the specimen mounting features; measuring a strain in a region of the fixture between the fixture mounting features; applying a second load to the fixture, the second load being substantially perpendicular to the first load; and controlling the second load in response to the measured strain.

The method may further comprise the step of applying a high cycle load to the specimen mounting features.

Preferably the measured strain is in the same direction as the second load.

Preferably the second load is controlled to keep the measured strain substantially constant.

Preferably the measured strain at a given time can be related to the coefficient of friction between the respective pressure faces of the specimen mounting features and the fixture mounting features at that time.

The strain-friction relationship may be derived using FE modelling techniques.

According to a second aspect of the invention, an apparatus for simulating life of a rotor blade mounting feature mounted in a complementary rotor disc mounting feature comprises two specimen mounting features each having portions defining pressure faces matching in profile respective faces of the rotor blade mounting feature; a fixture having two opposed mounting features each having portions defining pressure faces matching in profile respective faces of the rotor disc mounting feature, the specimen mounting features being mounted in the fixture mounting features; means for applying a first load to the specimen mounting features; means for measuring a strain in a region of the fixture between the fixture mounting features; means for applying a second load to the fixture, the second load being substantially perpendicular to the first load; and means for controlling the second load in response to the measured strain.

Preferably, means are also provided for applying high cycle loads to the specimen mounting features. The means for applying high cycle loads may comprise mechanical means or hydraulic means.

The region of the fixture between the fixture mounting features is preferably designed to achieve an optimal balance between strain sensitivity and rigidity.

The strain measurement means may comprise strain gauges, contacting extensometry or non-contacting extensometry.

The strain measurement means may also be used to indicate misalignment.

Strain measurement means may be provided on the specimen mounting features.

Means may be provided to heat at least the specimen mounting features.

BRIEF DESCRIPTION OF THE DRAWINGS

The invention will be more fully described, by way of example, with reference to the accompanying drawings in which.

DETAILED DESCRIPTION OF THE INVENTION

Figure 1:
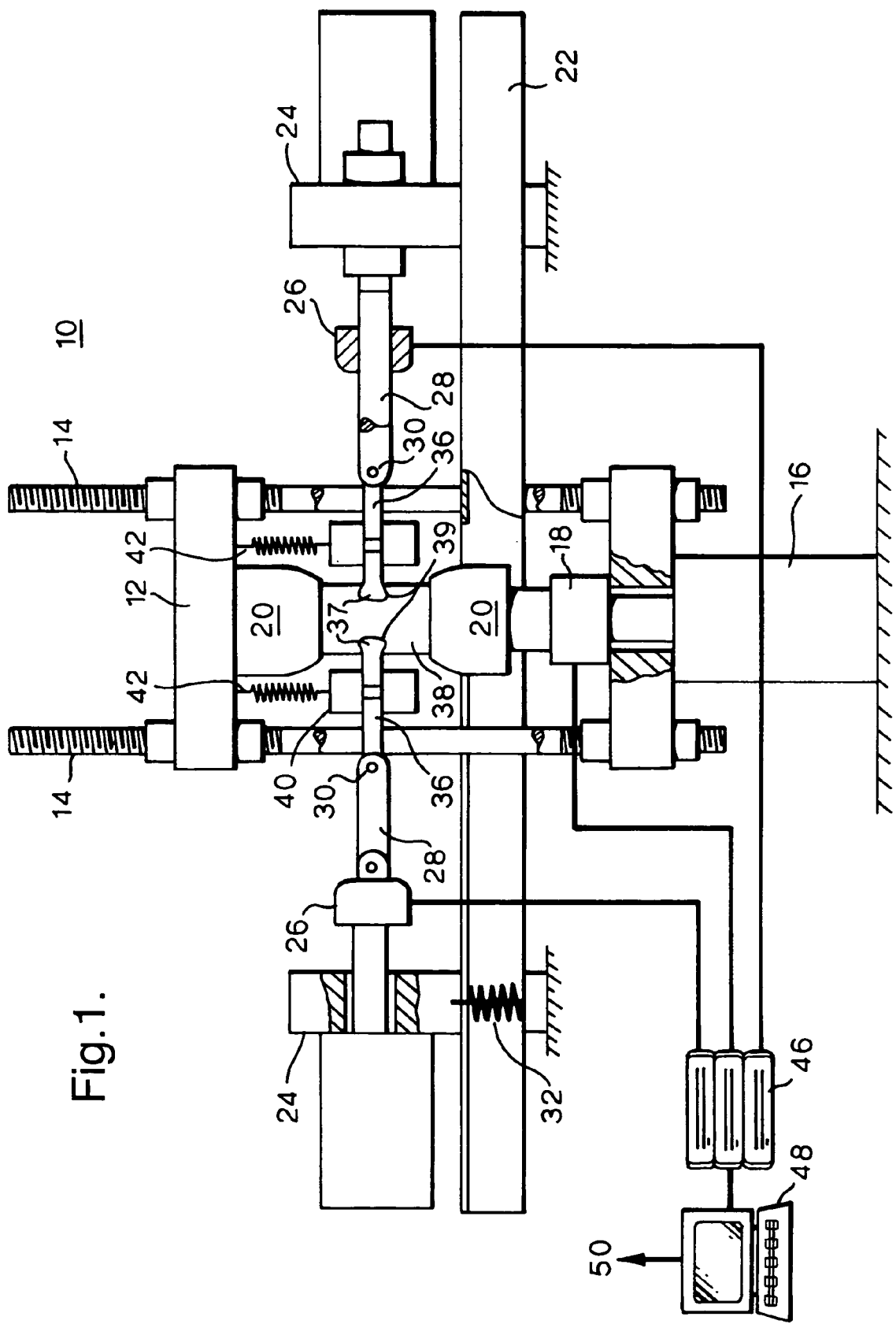
FIG. 1 shows a general view of an apparatus according to the invention.

Referring first to FIG. 1, a test machine shown generally at 10 has a load frame 12. Pillars 14 support a first hydraulic actuator 16 and a first load cell 18, and a pair of grips 20. Further structure 22 supports second hydraulic actuators 24, second load cells 26 and a pair of loading bars 28. Each loading bar 28 has a hole 30 near its end, into which a pin (not shown) can be fitted.

A fixture 38 is securely held between the grips 20 of the testing machine 10. The fixture 38 has two recesses 39 matching the profile of the disc slots whose behaviour is to be reproduced.

Two test specimens 36 have, at one end, a mounting feature 37 matching the profile of the blade whose behaviour is to be reproduced and, at the other end, a suitable hole permitting pin attachment of the test specimens 36 to the loading bars 28, in the conventional manner.

In operation, the first actuator 16 applies a load to the fixture 38. The applied load is measured by the first load cell 18. This loading represents the hoop stress in the disc, in the real component. The second actuators 24 apply loads to the test specimens 36. These loads are measured by the second load cells 26. These loads represent the centripetal loading of the rotor blades, in the real component.

The second actuators 24 are mounted on a floating carriage, supported on springs 32 (only one shown). These support the weight of the carriage, while permitting limited vertical movement. This permits the second actuators 24 to apply their loads without introducing undesired bending, even though the fixture 38 will move up and down slightly during the test as the load applied by the first actuator 16 decreases and increases.

The actuators 16 and 24 are controlled by a computer 48, which receives information from the load cells 18 and 26, via controllers 46, and sends controlling signals 50 to the actuators.

Attached to each test specimen 36 is an HCF shaker 40. Each HCF shaker 40 is attached to, but vibrationally isolated from, the load frame 12 by a spring 42. The load applied by the HCF shaker 40 represents the mechanical and aerodynamic vibrations in the blade, in the real component.

Figure 2:
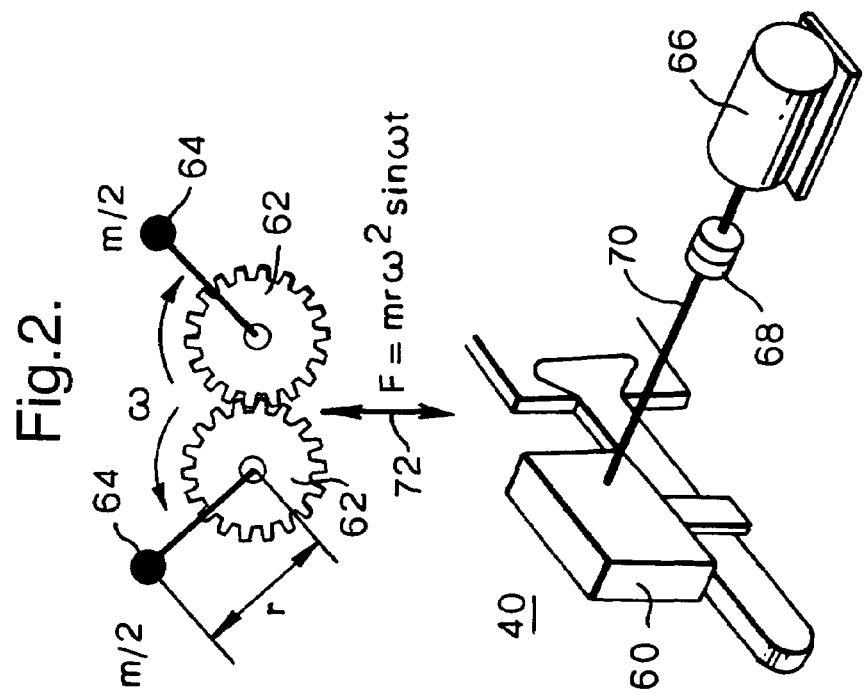
FIG. 2 illustrates the operation of a part of the apparatus of FIG. 1.

FIG. 2 illustrates the principles of operation of the HCF shaker 40. Within the casing 60 of the shaker 40, two intermeshing gear wheels 62 are mounted. Attached to each gear wheel 62, at a distance r from its centre, is an eccentric mass 64 of m/2. The angular disposition of the masses is as shown in the drawing, so that the assembly is symmetrical about a central vertical axis. When the gear wheels 62 are driven by an external electric motor 66, via a clutch/brake 68 and drive shaft 70, and the eccentric masses 64 are caused to rotate, a periodic reciprocating force F is set up, as shown by the arrow 72. The motor 66 and the clutch/brake 68 are controlled by signals 50 from the computer 48.

Figure 3:
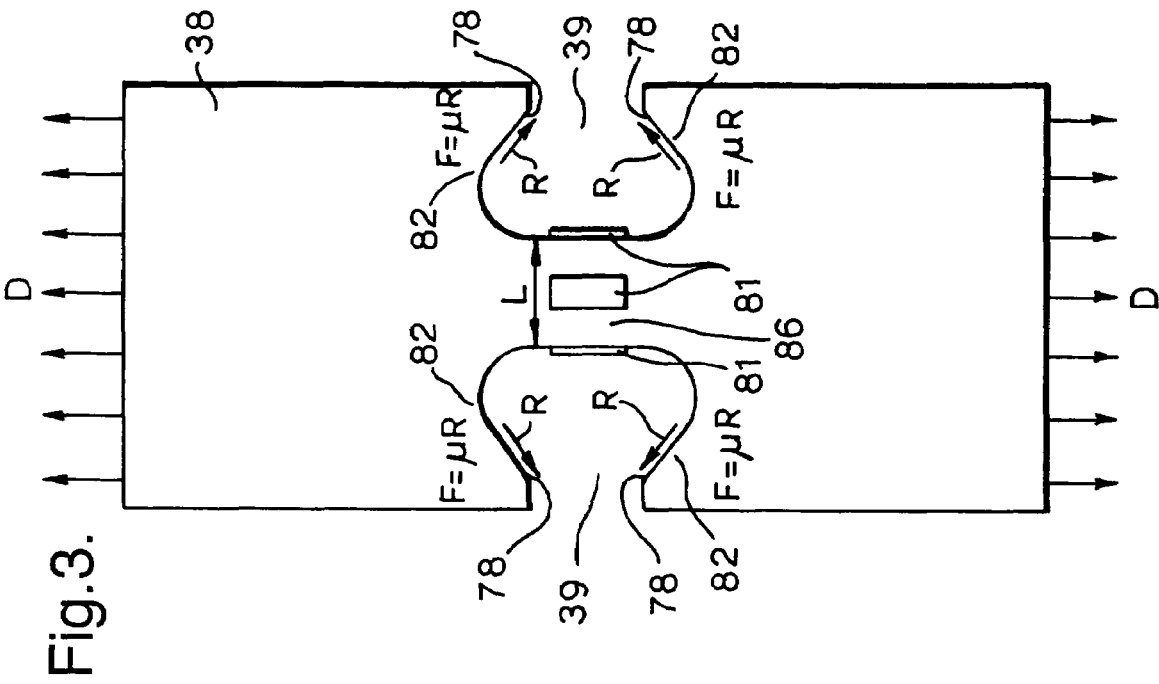
FIG. 3 shows a more detailed view of another part of the apparatus of FIG. 1.

Referring now to FIG. 3, the fixture 38 is shown in more detail. Four strain gauges 81 are mounted on the fixture (one is invisible behind the fixture).

By careful control of the rig loading, and the use of an arrangement of strain gauges on the disc specimen, it is possible to continuously monitor the evolution of contact flank friction during the test. Since the rig loading and geometry are representative of the real blade and disc, these results can be read across, directly, to service components.

In the real blade and disc, dilation of the disc slot is controlled by the elastic growth of the disc rim, under the influence of the disc hoop stress. Since this hoop stress is large, in comparison with the frictional forces and any blade 'wedging' effects, the strain at the bottom of the disc slot varies little with friction (i.e. the disc slot is essentially under strain-control). FIG. 3 shows the loading applied to the fixture 38, both directly and as a result of the mating test specimens 36.

When a load is applied to the test specimens 36 by the actuators 24 they move outwards in the fixture recesses 39, increasing the contact pressure R between the test specimen and fixture. This continues until limiting friction is reached, when the friction and reaction forces balance out the load applied to the blade specimen. The ligament 86 between the two fixture recesses is relatively thin compared to the rim of a disc. Thus, the force required to balance the force R results in appreciable strain increase in the disc ligament. This opening of the disc slots by the blade specimens is known as the 'wedging' effect.

At the start of the test, the load D on the fixture is set such that the relative sliding displacement, between the test specimen and the fixture, matches that in the real component, as determined from three-dimensional finite element (FE) modeling. During the test, the load D is then varied, such that the strain, measured at the disc slot bottom, remains constant. As the test progresses, wear of the coating leads to an increase in the friction coefficient μ on the dovetail contact flank 78. The blade specimen will slide out of the disc slot until limiting friction F is reached (as shown by the arrows 82). As friction increases then a lower contact pressure R is required to cause limiting friction, and thus the wedging effect is reduced, resulting in a drop is disc slot-bottom strain this can be compensated for by increasing the applied disc load D. From this change in the load required to achieve a given slot-bottom strain, the friction coefficient p on the contact flank can be determined, by interrogation of an FE model. Therefore, controlling the second load, via electric motor 66 and the clutch/brake 68 through the HCF shaker 40, in response to the measured strain of the fixture 38 in an attempt to maintain the measured strain constant is possible.

The width L of the fixture ligament 86 is designed such that the slot-bottom strain is sensitive to friction (for example a drop in strain of 30% would be achieved by going from 0.1 to 0.7 friction coefficient), whilst still ensuring the disc ligament 86 is stiff enough to prevent any alignment/bending problems for the rig. This is unlike the real component which is relatively stiff and insensitive to friction.

Finite Element (FE) analyses of the real fan blade and disc, and the bi-axial rig configuration, are required to define the test regime. In addition, these analyses cover the full range of friction levels likely to be seen, both in the real component and in the rig test. It is important that the same FE modelling standard (i.e. contact definition, friction level, element type, mesh density etc.) is used for both the specimen and real blade/disc analyses. This ensures that both stress level and relative sliding displacement can be accurately predicted.

Four basic parameters are required to set test conditions. These are:

1. The mean (DC) load being carried through the blade root resulting from centripetal loads—this determines the load applied to the test specimen.

2. The vibrational (AC) load applied to the blade root as a result of aerodynamic forcing—this determines the speed at which the HCF shakers will be run.

3. The relative movement between the blade and disc—this determines the strain which is required at the bottom of the disc slot and thus the load which should be applied to the disc specimen.

4. The number of vibration cycles per major cycle—this sets the duration of one cycle.

Typically 12 strain gauges are applied, four on each test specimen (not shown) and four on the fixture ligament (as shown in FIG. 3). These are used to ensure alignment of the rig, as well as ensuring the desired test conditions are achieved. The output of the strain gauges is recorded continuously during the test for later analysis.

It will be appreciated that modifications may be made to the apparatus without departing from the essence of the invention. For example, the test specimen mounting features 37 may be representative of a firtree root or any other conventional blade mounting feature. The HCF load may be applied by hydraulic means rather than by the mechanical arrangement described. A furnace or other heating means may be provided so that testing may be performed at elevated temperature. The strain measurement, either in the fixture ligament or in the test specimens, may be by contacting or non-contacting extensometry rather than by strain gauges.

We claim:

1. A method of simulating life of a rotor blade mounting feature mounted in a complementary rotor disc mounting feature, comprising the steps of providing two specimen mounting features each having portions defining pressure faces matching in profile respective faces of the rotor blade mounting feature;

providing a fixture having two opposed mounting features each having portions defining pressure faces matching in profile respective faces of the rotor disc mounting feature;

mounting the specimen mounting features in the fixture mounting features; applying a first load to the specimen mounting features;

measuring a strain in a region of the fixture between the fixture mounting features;

applying a second load to the fixture, the second load being substantially perpendicular to the first load;

controlling the second load in response to the measured strain.

2. A method as claimed in claim 1, further comprising the step of applying a high cycle load to the specimen mounting features.

3. A method as claimed in claim 1, in which the measured strain is in the same direction as the second load.

4. A method as claimed in claim 1, in which the second load is controlled to keep the measured strain substantially constant.

5. A method of simulating life of a rotor blade mounting feature mounted in a complementary rotor disc mounting feature, comprising the steps of providing two specimen mounting features each having portions defining pressure faces matching in profile respective faces of the rotor blade mounting feature;

providing a fixture having two opposed mounting features each having portions defining pressure faces matching in profile respective faces of the rotor disc mounting feature;

mounting the specimen mounting features in the fixture mounting features;

applying a first load to the specimen mounting features;

measuring a strain in a region of the fixture between the fixture mounting features wherein the measured strain at a given time can be related to the coefficient of friction between the respective pressure faces of the specimen mounting features and the fixture mounting features at that time;

applying a second load to the fixture, the second load being substantially perpendicular to the first load;

controlling the second load in response to the measured strain.

6. A method as claimed in claim 5, in which the strain-friction relationship is derived using FE modeling techniques.

7. An apparatus for simulating life of a rotor blade mounting feature mounted in a complementary rotor disc mounting feature, comprising two specimen mounting features each having portions defining pressure faces matching in profile respective faces of the rotor blade mounting feature;

a fixture having two opposed mounting features each having portions defining pressure faces matching in profile respective faces of the rotor disc mounting feature, the specimen mounting features being mounted in the fixture mounting features;

means for applying a first load to the specimen mounting features;

means for measuring a strain in a region of the fixture between the fixture mounting features;

means for applying a second load to the fixture, the second load being substantially perpendicular to the first load;

means for controlling the second load in response to the measured strain.

8. An apparatus as claimed in claim 7, in which means are provided for applying high cycle loads to the specimen mounting features.

9. An apparatus as claimed in claim 8, in which the means for applying high cycle loads comprise mechanical means or hydraulic means.

10. An apparatus as claimed in claim 7, in which the region of the fixture between the fixture mounting features is designed to achieve an optimal balance between strain sensitivity and rigidity.

11. An apparatus as claimed in claim 7, in which the strain measurement means comprise strain gauges, contacting extensometry or non-contacting extensometry.

12. An apparatus as claimed in claim 7, in which strain measurement means are provided on the specimen mounting features.

13. An apparatus as claimed in claim 7, in which means are provided to heat at least the specimen mounting features.

14. An apparatus for simulating life of a rotor blade mounting feature mounted in a complementary rotor disc mounting feature, comprising two specimen mounting features each having portions defining pressure faces matching in profile respective faces of the rotor blade mounting feature;

a fixture having two opposed mounting features each having portions defining pressure faces matching in profile respective faces of the rotor disc mounting feature, the specimen mounting features being mounted in the fixture mounting features:

means for applying a first load to the specimen mounting features;

means for measuring a strain in a region of the fixture between the fixture mounting features wherein the strain measurement means are also used to indicate misalignment;

means for applying a second load to the fixture, the second load being substantially perpendicular to the first load; means for controlling the second load in response to the measured strain.

* * * * *